(12) United States Patent
Armwood

(10) Patent No.: US 8,231,156 B2
(45) Date of Patent: Jul. 31, 2012

(54) CONTACT LENS APPLICATION DEVICE AND METHOD

(76) Inventor: Kenneth Armwood, Sparta, NJ (US)

(*) Notice: Subject to any disclaimer, the term of this patent is extended or adjusted under 35 U.S.C. 154(b) by 0 days.

(21) Appl. No.: 13/161,551

(22) Filed: Jun. 16, 2011

(65) Prior Publication Data
US 2012/0172886 A1    Jul. 5, 2012

Related U.S. Application Data

(60) Provisional application No. 61/429,259, filed on Jan. 3, 2011.

(51) Int. Cl.
*A61F 9/00* (2006.01)
(52) U.S. Cl. .......................... 294/1.2; 294/187
(58) Field of Classification Search .............. 294/1.2, 294/187; 359/815; 351/219, 247; 604/295–302
See application file for complete search history.

(56) References Cited

U.S. PATENT DOCUMENTS

| | | | | |
|---|---|---|---|---|
| 676,379 A * | 6/1901 | Young | ................ | 601/37 |
| 852,827 A * | 5/1907 | Dorment | ................ | 601/13 |
| 1,437,435 A * | 12/1922 | Maier | ................ | 604/297 |
| 3,879,076 A * | 4/1975 | Barnett | ................ | 294/1.2 |
| 3,934,914 A | 1/1976 | Carruthers | | |
| 4,123,098 A | 10/1978 | Shoup | | |
| 4,193,622 A * | 3/1980 | Overman | ................ | 294/1.2 |
| 4,221,414 A | 9/1980 | Schrier | | |
| 4,286,815 A | 9/1981 | Clark | | |
| 4,326,742 A * | 4/1982 | Ingram | ................ | 294/1.2 |
| 4,703,964 A * | 11/1987 | Ranani | ................ | 294/219 |
| 5,050,918 A | 9/1991 | Kolze | | |
| 5,456,508 A | 10/1995 | Kozar | | |
| 7,784,936 B2 * | 8/2010 | Stinson | ................ | 351/158 |
| 2005/0162127 A1 | 7/2005 | Hutchins | | |
| 2007/0236946 A1 | 10/2007 | Petrakis | | |

* cited by examiner

*Primary Examiner* — Dean Kramer
(74) *Attorney, Agent, or Firm* — Daniel Boudwin

(57) ABSTRACT

A pressure application and removal device is provided for the purpose of assisting insertion of contact lenses. The device comprises a frame portion, two contact lens holders, a pressurizing assembly, and a liquid delivery assembly. The frame portion has the structure of standard eyeglasses frames and rests on a user's ears and nose. The contact lens holders are formed of wash cups that retain contact lenses along the inside of their concave surface. Fluid conduits extend from an apex of the wash cups to a flexible ball in the center of the device. When said ball is depressed, a positive pressure or vacuum is generated to facilitate insertion and removal of contact lenses to or from a user's eye. A second flexible ball may be filled with liquid. When the ball is compressed liquid flows through a second set of conduits into the eye of a user.

4 Claims, 2 Drawing Sheets

CONTACT LENS APPLICATION DEVICE AND METHOD

CROSS REFERENCE TO RELATED APPLICATION

This application claims the benefit of U.S. Provisional Application No. 61/429,259 filed on Sep. 3, 2010, entitled "Medical Contact Replacement."

BACKGROUND OF THE INVENTION

1. Field of the Invention

The present invention relates to an assistive device for optical lens insertion or removal, more specifically it relates to a device for inserting or removing contact lenses that may be attached to a pair of glasses to provide a stabilizing means.

Contact lenses are a commonly used ophthalmological device for the purpose of correcting certain types of poor visual acuity. Since their first production in the late 1800's they have frustrated users with their difficult insertion and removal. Originally contacts were rigid and did not conform well to the shape of a user's eye. As a result the lenses were hard to put in and often came out during the course of regular use. As contact lens manufacturing technology has progressed, the lenses have become soft, moist and flexible to promote greater conformity, comfort, and convenience. Despite these improvements to their construction, contact lenses remain difficult for many users to insert and remove. They are generally used by men and women with poor visual acuity who may have trouble seeing accurately enough to safely insert or remove the contact lenses.

There have been many devices created over the years to assist wearers of contacts with the application of their lenses. Most of these devices are cylindrical in shape with a lens holding means and a pressurizing means such as a flexible ball or tube. These devices suffer the common drawback of needing a user to stabilize the device by holding it in his or her hand. Hand held devices do not possess the stability and support necessary to reduce risk of eye injuries. Additionally, these devices do not provide a stable means for application of medical liquids into a user's eye.

2. Description of the Prior Art

The prior art discloses a variety of devices for insertion and removal of optical contact lenses. These devices have familiar design and structural elements for the purposes of assisting wears of contact lenses with the insertion and removal of those lenses; however they are not adapted for providing a balanced support structure such as a pair of eyeglasses, or for administration of medical fluids into the eye.

Carruthers, U.S. Pat. No. 3,934,914 discloses a contact lens insertion and removal device having a cylindrical tube, a lens holding cup at one end, a light transmitting portion at the opposite end. Opposing lateral sides of said tube are flexible to create changes in pressure that facilitate insertion or removal of a contact lens from a user's eye.

Shoup, U.S. Pat. No. 4,123,098 discloses a device for removing contact lenses comprising a flexible bulb operatively attached to a contact lens holder by a cylindrical tube. Said bulb is depressed to create the pressure necessary to insert or remove a contact lens.

Schrier, U.S. Pat. No. 4,221,414 discloses a contact lens insertion and removal device comprising a bifurcated body portion having angled contact lens holders disposed at the end of said bifurcations. The angled bifurcations may be placed against an eye while a contact lens is being held, to tilt the lens into place on the surface of the eye.

Clark, U.S. Pat. No. 4,286,815 discloses a device for removing or inserting contact lenses from an eye comprising a suction cup secured to a tunnel extension and operatively attached to a vacuum means by a collapsible tubular portion.

Kolze, U.S. Pat. No. 5,050,918 discloses a device for inserting or removing contact lenses comprising a concave lens holding portion attached to a rigid fluid conduit that allows air to flow to and from a flexible ball secured to the conduit's opposite end. Said ball is compressed to create pressure for inserting or removing contacts from the surface of the idea. A mirror arm and a support arm are secured to the rigid conduit to offer guidance to a user.

Kozar, U.S. Pat. No. 5,456,508 discloses a device for removing contact lenses having a concave lens holder attached to a cylindrical tunnel. Said cylindrical tunnel having a flexible ball disposed along its length and another at its end. Said balls may be used to create vacuum pressure for removing contacts from the eye of a user.

The prior art patents describe alternative structures for application of contact lenses, and are substantially different from the present invention in intent and function. In particular, the prior art does not disclose a structural support in the form of eye glasses, nor does it disclose a liquid dispersing means for ready application of liquids into the eye during contact insertion and removal. The current invention relates to a device for insertion and removal of contact lenses from a user's cornea that provides a stabilizing means and allows a user to insert medical liquids into the eye. It substantially diverges in structural elements from the prior art, consequently it is clear that there is a need in the art for an improvement to the existing contact lens insertion and removal devices. In this regard the instant invention substantially fulfills these needs.

SUMMARY OF THE INVENTION

In view of the foregoing disadvantages inherent in the known types of contact lens insertion and removal devices now present in the prior art, the present invention provides a new stabilizing eye glass structure wherein the same can be utilized for providing convenience for the user when inserting or removing medical contact lenses. The medical contact lens insertion and removal device comprises a frame portion, two contact lens holders, a pressurization assembly, and a liquid delivery assembly. The frame portion is a pair of eyeglasses having two lenses attached along their outside edges to earpieces. The earpieces secure the device to a user's head allowing the user to maintain the use of both hands while utilizing the device.

Two wash cups serve as contact lens holders. The cups are secured to the lens portions of the device's frame at the apex of their convex outer surfaces. Contact lenses are removably secured to the apex of the concave inner surfaces of the holders while the lenses await insertion. The contacts are held in place by pressure generated by the pressurization assembly. This pressurization assembly comprises a flexible ball located between the lens holders that is connected on each side to a small conduit extending to the backside of each lens holder. When the ball is compressed, positive pressure is created that can be used to insert contact lenses onto the user's eye. When compression is released, a vacuum is created to remove contact lenses and temporarily secure them in the holders.

The liquid delivery assembly consists of a second flexible ball having two fluid conduits extending from its sides to the inside of the lens holders. The flexible ball may be filled with a liquid such as medication, contact lens solution, or saline eye drops. Compression of the flexible ball by a user wearing the device, results in the liquid being applied to the user's cornea.

It is therefore an object of the present invention to provide a new and improved contact lens insertion and removal device that has all of the advantages of the prior art and none of the disadvantages.

Another object of the present invention is to provide a new and improved contact lens insertion and removal that comprises glasses worn on the face of a user. The glasses provide a stabilizing structure allowing the user to have the use of both hands while operating the device.

Yet another object of the present invention is to provide a new and improved contact lens insertion and removal device that includes a flexible ball filled with liquid or medicine. The liquid or medicine may be applied to the eyes of a user by compression of the flexible ball.

Still another object of the present invention is to provide a new and improved contact lens insertion and removal device that provides a means for holding two contact lenses simultaneously to promote efficient consecutive insertion or removal of the same.

Another object of the present invention is to provide a new and improved contact lens insertion and removal device that is has resilient and durable construction.

Other objects, features and advantages of the present invention will become apparent from the following detailed description taken in conjunction with the accompanying drawings.

BRIEF DESCRIPTIONS OF THE DRAWINGS

The above invention will be better understood and the objects set forth above as well as other objects not stated above will become more apparent after a study of the following detailed description thereof. Such description makes use of the annexed drawings wherein.

DETAILED DESCRIPTION OF THE INVENTION

Figure 1:
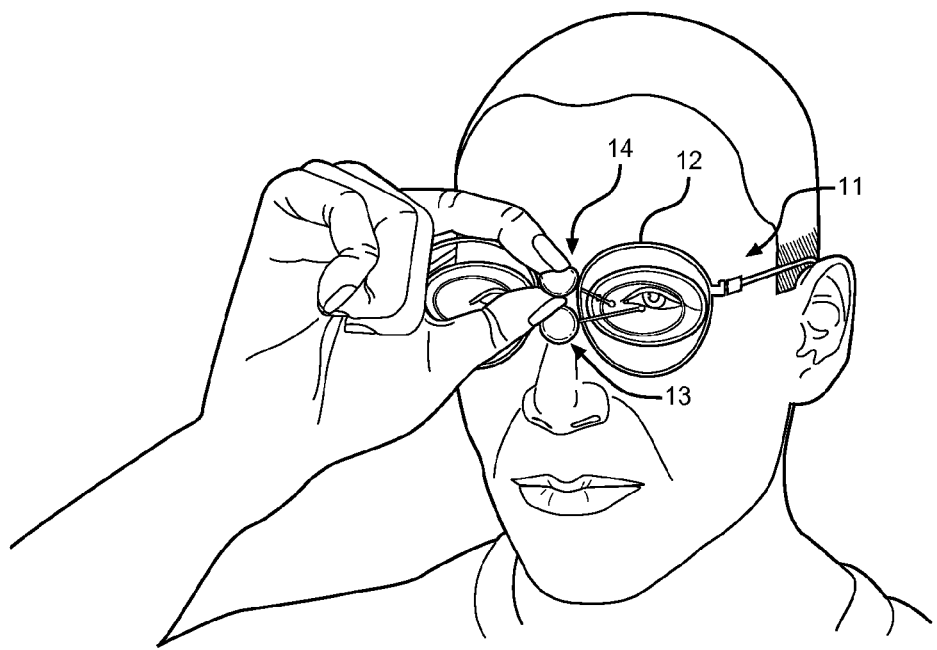
FIG. 1 is a perspective view of a preferred embodiment of the present invention in use.

Reference is made herein to the attached drawings. Like reference numerals are used throughout the drawings to depict like or similar elements of the claimed contact lens insertion and removal device. For the purposes of presenting a brief and clear description of the present invention, the preferred embodiment will be discussed as used for insertion and removal of contact lenses from the surface of a user's eyes. This is for representative purposes only and should not be considered to be limiting in any respect.

Referring now to FIG. 1, there is shown a user operating a contact lens insertion and removal device according to the present invention. The device comprises a frame portion 11, two contact lens holders 12, a pressurization assembly 13, and a liquid delivery assembly 14. It sits on the face of a user with said frame portion 11 resting on and behind the ears and said pressurization assembly 13 resting on the nose. In this manner the device is secured to a user's head to provide stability and support while the device is in use.

Figure 2:
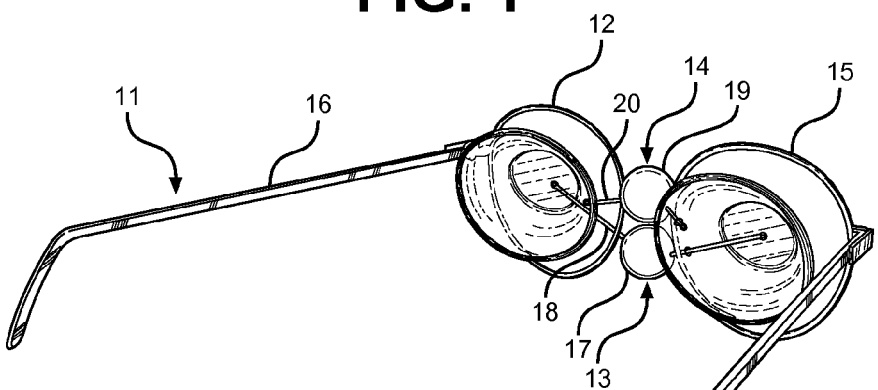
FIG. 2 is a perspective view of a preferred embodiment of the present invention.
Figure 3:
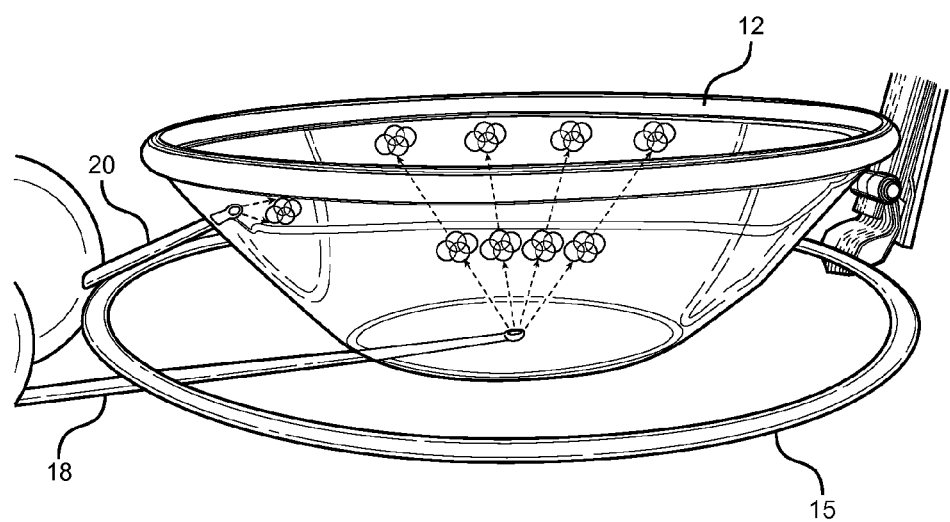
FIG. 3 is a magnified view of a contact lens holder according to the present invention.

Referring now to FIGS. 2 & 3, there is shown a perspective view and a magnified view of the present invention. The frame portion 11 comprises a pair of eyeglasses with two geometrically shaped lenses 15 and two earpieces 16. Said earpieces 16 extend from the outer rim of said geometrically shaped lenses 15 to the back of a user's ear, thus securing the device to a user's head. The frame may be made from any materials used for eyeglass frames such as plastic, metal, metal alloys, wood, or a combination thereof. Any translucent durable material such as plastic, polycarbonate, or glass may be used in construction of the geometrically shaped lenses 15.

The contact lens holders 12 are two wash cups having a convex outer surface and a concave inner surface. Said lens holders 12 are affixed at the apexes of their convex outer surface to the inner faces of the geometrically shaped lenses 15. Contact lenses are held in place at the apexes of the concave inner surfaces of said lens holders by a vacuum generated by the pressurization assembly 13. The holders are sized to fit snuggly between a user's brow-bone and cheek-bone and may be constructed from the same materials as the geometrically shaped lenses 15.

The pressurization assembly 13 comprises a flexible ball 17 and two attached conduits 18. The flexible ball 17 is disposed between the geometrically shaped lenses 15 and rests on a user's nose (as shown in FIG. 1). Extending from the sides of said flexible ball 17 to the apex area of the lens holders 12 are two fluid conduits 18. When the ball 17 is compressed by a user air flows outward through the conduits 18 creating positive pressure on a contact lens removably secured in the lens holder 12. Upon decompression of the flexible ball 17 a vacuum is generated, resulting in a gentle suction that can be used to remove a contact lens from a user's eye and secure the same within the contact lens holder 12.

A fluid assembly comprising a flexible ball 19 and two fluid conduits 20 facilitates application of liquids into a user's eye. Said flexible ball 19 is disposed between the geometrically shaped lenses 12 above the flexible ball 17 of the pressurization assembly 13. The conduits 20 extend from the sides of the ball 19 to the contact lens holders 12. The open ends of said conduits are positioned along the concave surface of the lens holders 12 opposed to a user's eye. Fluids such as medicine, contact lens solution, or saline eye drops may be stored in the flexible ball 19. When the ball 19 is compressed fluid is pushed through the conduits 20 onto the cornea of a user.

In alternate embodiments the device may come without the frame portion. The embodiment comprises the contact lens holders, pressurization assembly, liquid delivery assembly, and means for securing the device to the ear pieces of a user's eye glasses (not shown in the FIGs). This embodiment increases the convenient portability of the device.

In use an individual compresses the pressurization ball 17 and fits the convex side of a contact lens into the concave apex of a contact lens holder 12. When both contact lenses have been inserted into the holders 12 the user releases the flexible ball 17 generating the vacuum that secures said contact lenses to the contact lens holders 12. The user then places the earpieces 16 over his or her ears and rests the flexible ball 17 of the pressurization assembly on the nose. Eye drops may be applied to the eye of a user by compressing the liquid delivery ball 19. A user then compresses the pressurization ball 17 to exert force on the contact lenses and push them gently onto the cornea of a user's eye. This process may be reversed to remove the contact lenses.

With respect to the above description then, it is to be realized that the optimum dimensional relationships for the parts of the invention, to include variations in size, materials, shape, form, function and manner of operation, assembly and use, are deemed readily apparent and obvious to one skilled in the art m, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim the following:

1. A device for assisting in the insertion and removal of contact lenses comprising:
    a frame portion having two geometrically shaped lenses secured along their outer rims to earpieces;
    a pair of wash cups mounted to the inner surfaces of said geometrically shaped lenses,
    said wash cups being adapted to receive and retain a pair of contact lenses;
    a pressurization assembly comprising a flexible pressurization ball operatively connected to two pressurization conduits,
    said pressurization conduits extending from said flexible pressurization ball to the interior of said wash cups;
    and a liquid delivery assembly comprising a flexible fluid filled ball operatively attached to two fluid conduits,
    said fluid conduits extending from said flexible fluid filled ball to an interior of said wash cups.

2. A device that is removably securable to a pair of glasses, for assisting in the insertion and removal of contact lenses comprising:
    a pair of wash cups adapted to receive and retain a pair of contact lenses;
    a pressurization assembly comprising a flexible pressurization ball operatively connected to two pressurization conduits,
    said pressurization conduits extending from said flexible pressurization ball to the interior of said wash cups;
    a liquid delivery assembly comprising a flexible fluid filled ball operatively attached to two fluid conduits,
    said fluid conduits extending from said flexible fluid filled ball to the interior of said wash cups.

3. A method for inserting contact lenses onto the surface of an eye comprising the steps of
    compressing a flexible pressurization ball to expel air from said ball through a set of conduits operatively attached to a pair of wash cups;
    placing a pair of contact lenses along an apex of a concave inner surface of said wash cups,
    releasing said flexible pressurization ball to create a vacuum against said contact lenses;
    securing a contact lens insertion device to a user so that said wash cups are fitted against a user's eye sockets;
    compressing said flexible pressurization ball a second time to generate positive pressure on the back of said contact lenses,
    said pressure being sufficient to push said contact lenses onto the corneas of a user.

4. The method of claim 3, further comprising:
    compressing a flexible fluid filled ball to force liquid medication through a set of conduits and into eyes of a user.

* * * * *